United States Patent [19]
Schulze et al.

[11] Patent Number: 5,876,401
[45] Date of Patent: *Mar. 2, 1999

[54] ELECTROSURGICAL HEMOSTATIC DEVICE WITH ADAPTIVE ELECTRODES

[75] Inventors: Dale R. Schulze, Lebanon; William D. Fox, New Richmond; David Yates, West Chester; Anil Nalagatla, Cincinnati, all of Ohio

[73] Assignee: Ethicon Endo Surgery, Inc., Cincinnati, Ohio

[ * ] Notice: The term of this patent shall not extend beyond the expiration date of Pat. No. 5,693,057.

[21] Appl. No.: 843,195

[22] Filed: Apr. 14, 1997

Related U.S. Application Data

[63] Continuation of Ser. No. 421,353, Apr. 12, 1995, Pat. No. 5,693,051, which is a continuation-in-part of Ser. No. 95,797, Jul. 22, 1993, Pat. No. 5,403,312.

[51] Int. Cl.⁶ .................................................. A61B 17/36
[52] U.S. Cl. ................................. 606/51; 606/41; 606/42
[58] Field of Search ........................... 606/41, 42, 45–52; 607/100–102; 600/372, 374

[56] References Cited

U.S. PATENT DOCUMENTS

| | | |
|---|---|---|
| 4,016,881 | 4/1977 | Rioux et al. . |
| 4,041,952 | 8/1977 | Morrison, Jr. et al. . |
| 5,190,541 | 3/1993 | Abele et al. . |
| 5,403,312 | 4/1995 | Yates et al. . |
| 5,443,463 | 8/1995 | Stern et al. . |
| 5,496,312 | 3/1996 | Klicek . |
| 5,626,578 | 5/1997 | Tihon ........................................ 606/48 |
| 5,693,051 | 12/1997 | Schulze et al. ........................... 606/51 |
| 5,735,848 | 4/1998 | Yates et al. ............................... 606/48 |

FOREIGN PATENT DOCUMENTS

| | | |
|---|---|---|
| 05894A3 | 3/1994 | European Pat. Off. . |
| 0640315A1 | 1/1995 | European Pat. Off. . |
| 0640317A1 | 1/1995 | European Pat. Off. . |
| 4130064A1 | 3/1993 | Germany . |
| WO 94/24949 | 10/1994 | WIPO . |

*Primary Examiner*—Michael Peffley

[57] ABSTRACT

An electrosurgical instrument is provided for cauterization and/or welding of tissue of varying impedance, thickness, compressibility, density, vascularity, etc., especially in the performance of endoscopic procedures. The instrument provides two electrodes of different electrical potentials. One electrode is moveable with respect to the other electrode to vary the distances between the electrodes and thus the impedance of the tissue as presented to the generator. The electrode distances may be varied by an automated or user controlled device.

21 Claims, 11 Drawing Sheets

ELECTROSURGICAL HEMOSTATIC DEVICE WITH ADAPTIVE ELECTRODES

This is a continuation, of application Ser. No. 08/421,353 filed Apr. 12, 1995, now U.S. Pat. No. 5,693,051, which is hereby incorporated by reference, which is a continuation-in-part to U.S. application Ser. No. 095,797, filed on Jul. 22, 1993, now U.S. Pat. No. 5,403,312 incorporated herein by reference.

FIELD OF THE INVENTION

This invention relates to an electrosurgical instrument for cauterization, coagulation and/or tissue welding in the performance of surgical procedures, especially endoscopic procedures.

BACKGROUND OF THE INVENTION

Surgical procedures requiring cutting of tissue can cause bleeding at the site of the cutting. Various techniques have been adapted to control bleeding with varying degrees of success such as, for example, suturing, applying clips to blood vessels, and stapling, as well as electrocautery and other tissue heating techniques. Advances in tissue joining or welding, tissue repair and wound closure also have permitted surgical procedures previously not possible or too risky.

Surgical staplers have been used for tissue security, joining and approximation, and to provide hemostasis in conjunction with tissue cutting. Such devices include, for example, linear and circular cutting and stapling instruments. Typically, a linear cutter has parallel rows of staples with a slot for a cutting means to travel between the rows of staples. This type of surgical stapler secures tissue for improved cutting, joins layers of tissue, and provides hemostasis by applying parallel rows of staples to layers of surrounding tissue as the cutting means cuts between the parallel rows.

Electrocautery devices have been used for effecting improved hemostasis by heating tissue and blood vessels to cause coagulation or cauterization. Monopolar devices utilize one electrode associated with a cutting or cauterizing instrument and a remote return electrode, usually adhered externally to the patient. More recently, bipolar instruments have been used because the cauterizing current is generally limited to tissue between two electrodes of a tissue treating portion of an instrument.

Bipolar forceps have been used for cutting and/or coagulation in various procedures. Generally, bipolar forceps grasp tissue between two poles and apply electrical current through the grasped tissue. Bipolar forceps, however, have certain drawbacks, some of which include the tendency of the current to arc between poles when tissue is thin or the forceps to short when the poles of the forceps touch. The use of forceps for coagulation is also very technique dependent and the forceps are not adapted to simultaneously cauterize a larger area of tissue. Furthermore, forceps tend to cause areas of thermal spread, i.e., dissipation of heat outside of area defined by grasping or engaging surfaces of the forceps.

When using RF energy in electrosurgical devices, there may be an optimal range of tissue impedances that results in the best or optimal energy delivery for the output characteristics of the particular generator to which the impedance load is presented.

Generally, the optimal range is related to the principal that where the source and load impedances are matched, the transfer of power from the source to the load is maximized. Further, the power output for a given generator decreases at a predictable rate as impedance of the load, i.e., tissue, falls off of the source impedance.

The optimal range is defined herein as the range of load impedances at which the power transfer from the generator is sufficient to achieve the intended result, i.e., controlled coagulation, cauterization, or tissue welding. The optimal range may vary from application to application or from generator to generator.

It is believed that tissue impedance varies depending on a number of parameters which may include: tissue type, liquid content, tissue condition (i.e., coagulated or uncoagulated), tissue thickness, the amount of tissue compression, the size and length of the flow path of electrical current through the tissue, and energy frequency applied to tissue.

Additionally, for a given area or volume of tissue,-the impedance model of the tissue is dynamic due to the fact that tissue impedance changes as tissue is heated and begins to coagulate, thus effecting the current flow pattern through the area or volume of tissue as coagulating current is delivered to the tissue. It is also believed that the tissue thickness typically changes as it is electrosurgically treated, because, for example, as water escapes in the form of steam or vapor the volume of the material grasped by the instrument is reduced. Depending on the specific end effector configuration, this could provide an additional variable in the impedance model of the tissue if in the particular end effector tissue thickness were to effect the length of the current path and/or the amount of compression applied to the tissue.

Thus, it is desirable to provide an electrosurgical device which can efficiently provide hemostasis in multiple tissue types and thicknesses, e.g., in fleshy or vascular tissue areas, and high, low or combination impedance tissues. Hemostasis is used herein, generally, to mean the arresting of bleeding including by coagulation, cauterization and/or tissue joining or welding.

It is further desirable to provide a device which adapts to the changing impedance and/or tissue thicknesses as the tissue is being treated, so that the impedance presented to the generator is within an optimal range.

SUMMARY OF THE INVENTION

It is therefore an object of the invention to provide an electrosurgical method and device which optimize the efficiency of a tissue treating energy by configuring the electrodes of the end effector-to adapt to the type, thickness, impedance, or other parameter of tissue to be engaged by the end effector. This allows the instrument to bring a range of expected tissue impedance levels within an optimal load impedance range for the generator, and to obtain a desired result, e.g. controlled coagulation, cauterization, or tissue welding.

Accordingly, one embodiment of the present invention provides an adjustable device in which the distance between the opposite poles or electrodes of a tissue grasping or clamping device may be adjusted. The device may be adapted to compensate for tissue thickness, various tissue types or applications of the device.

Also, an embodiment of the present invention provides a device which dynamically or continuously adapts to the changing impedance and thickness of tissue as the tissue is being coagulated so that energy is efficiently delivered to the tissue. The device may be adjusted continuously or at intervals during a period of treatment.

In a preferred embodiment the adjustment means may be an automated or user actuated mechanical device.

The device may be used in various instruments using therapeutic electrosurgical energy such as, for example, tissue fastening devices, e.g. staplers, clip appliers, suturing devices, etc. Other end effector configurations may be used such as, for example, cutting devices, linear or circular cutting and stapling devices, etc.

These and other objects of the invention will be better understood from the following attached Detailed Description of the Drawings, when taken in conjunction with the Detailed Description of the invention.

DETAILED DESCRIPTION OF THE DRAWINGS

DETAILED DESCRIPTION OF THE PREFERRED EMBODIMENTS

Figure 5:
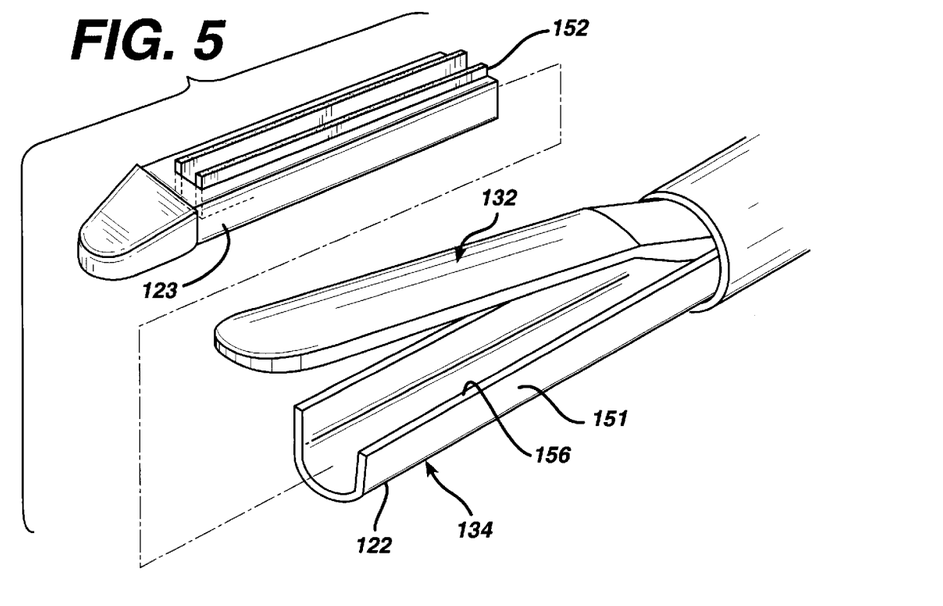
FIG. 5 is a perspective partial breakaway, partial exploded view of an alternative embodiment of a clamping device of the present invention.
Figure 6:
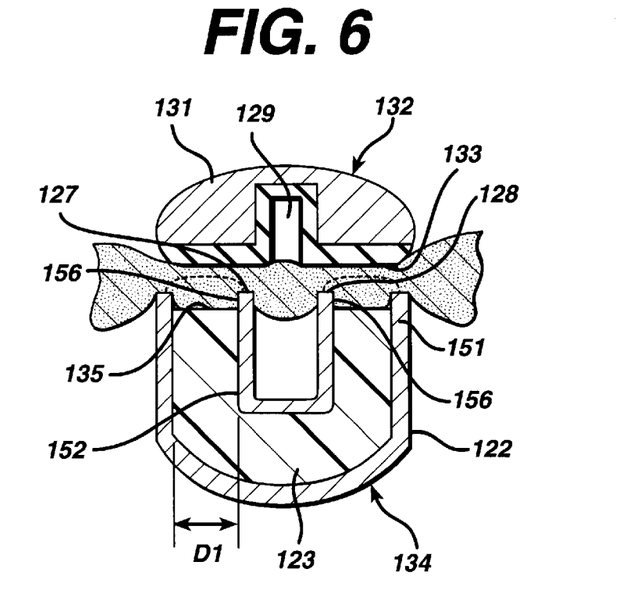
FIG. 6 is a front cross-sectional view of the device illustrated in FIG. 5 along the lines 6—6 with a cartridge for relatively thick tissue inserted into the end effector.
Figure 7:
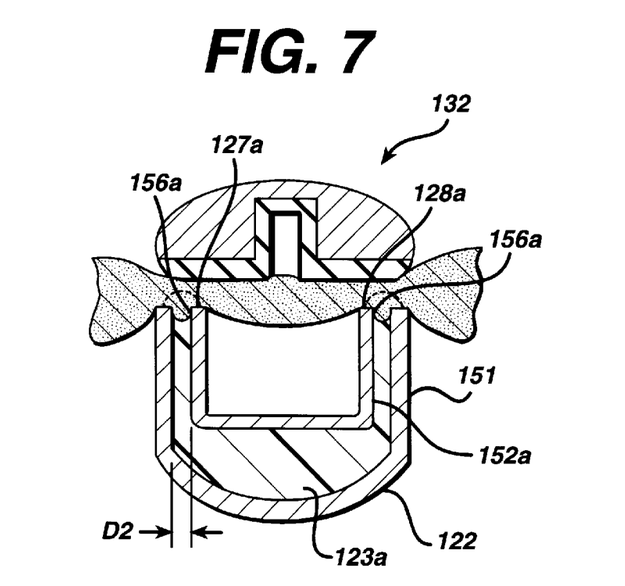
FIG. 7 illustrates a front cross-sectional view of the device illustrated in FIG. 5 along lines 6—6 with a cartridge for relatively thinner tissue than in FIG. 6.
Figure 8:
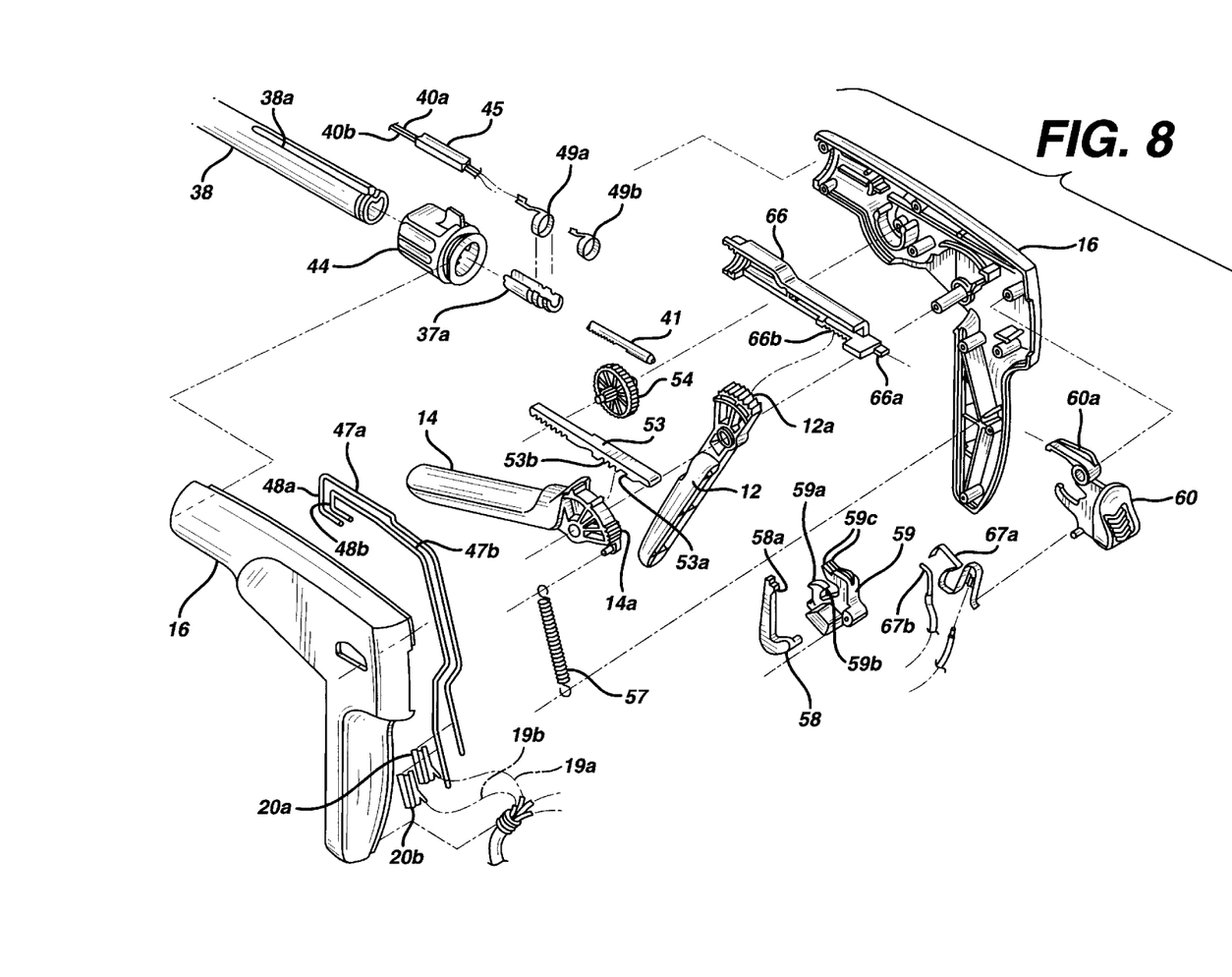
FIG. 8 is an exploded perspective view of the proximal handle portion of the instrument of FIG. 1.
Figure 9:
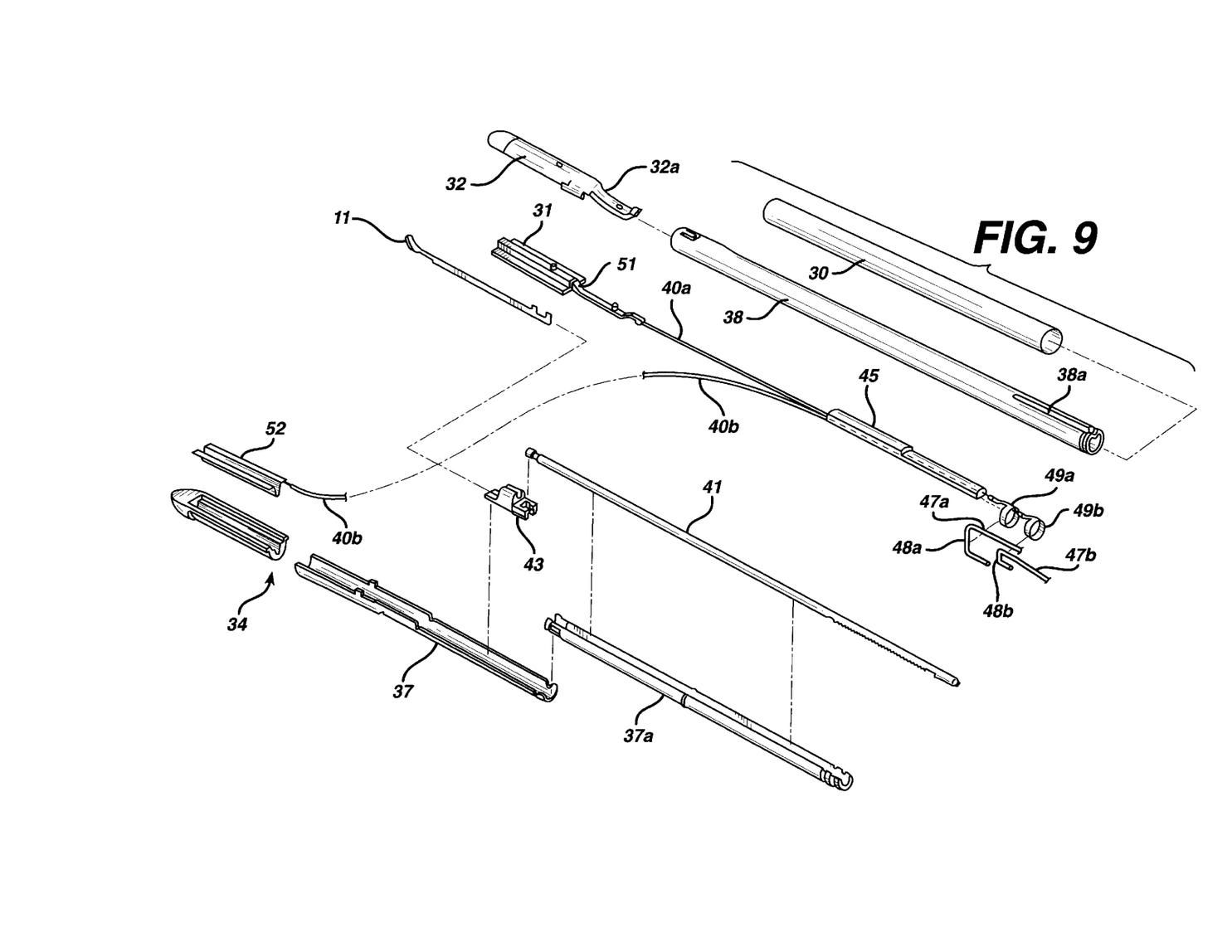
FIG. 9 is an exploded perspective view of the intermediate and distal portion of the instrument of FIG. 1.
Figure 10:
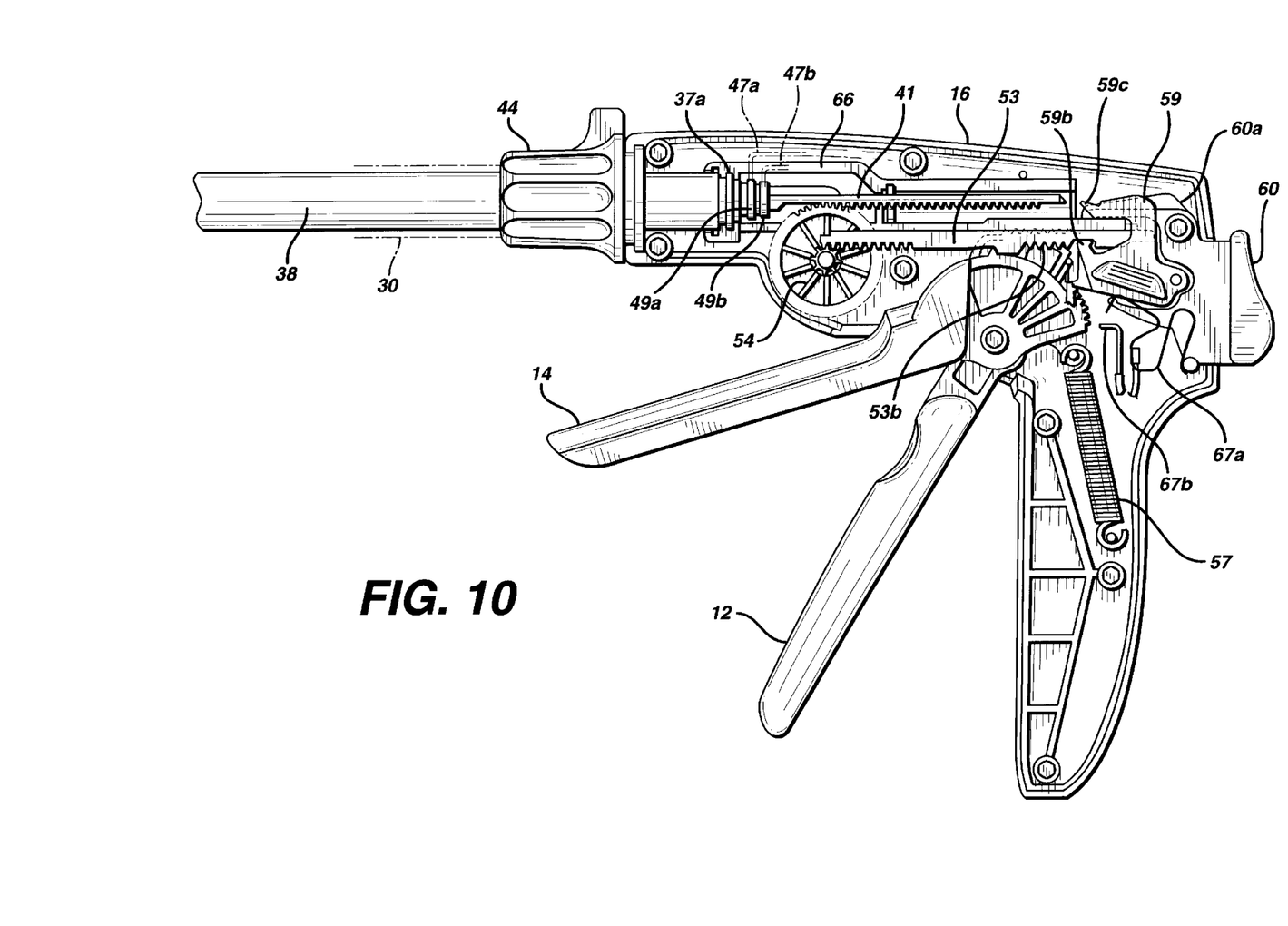
FIG. 10 is a side elevational view of the proximal handle portion in a first, open position of the instrument of FIG. 1, shown with the left side handle cover and wireforms removed.
Figure 11:
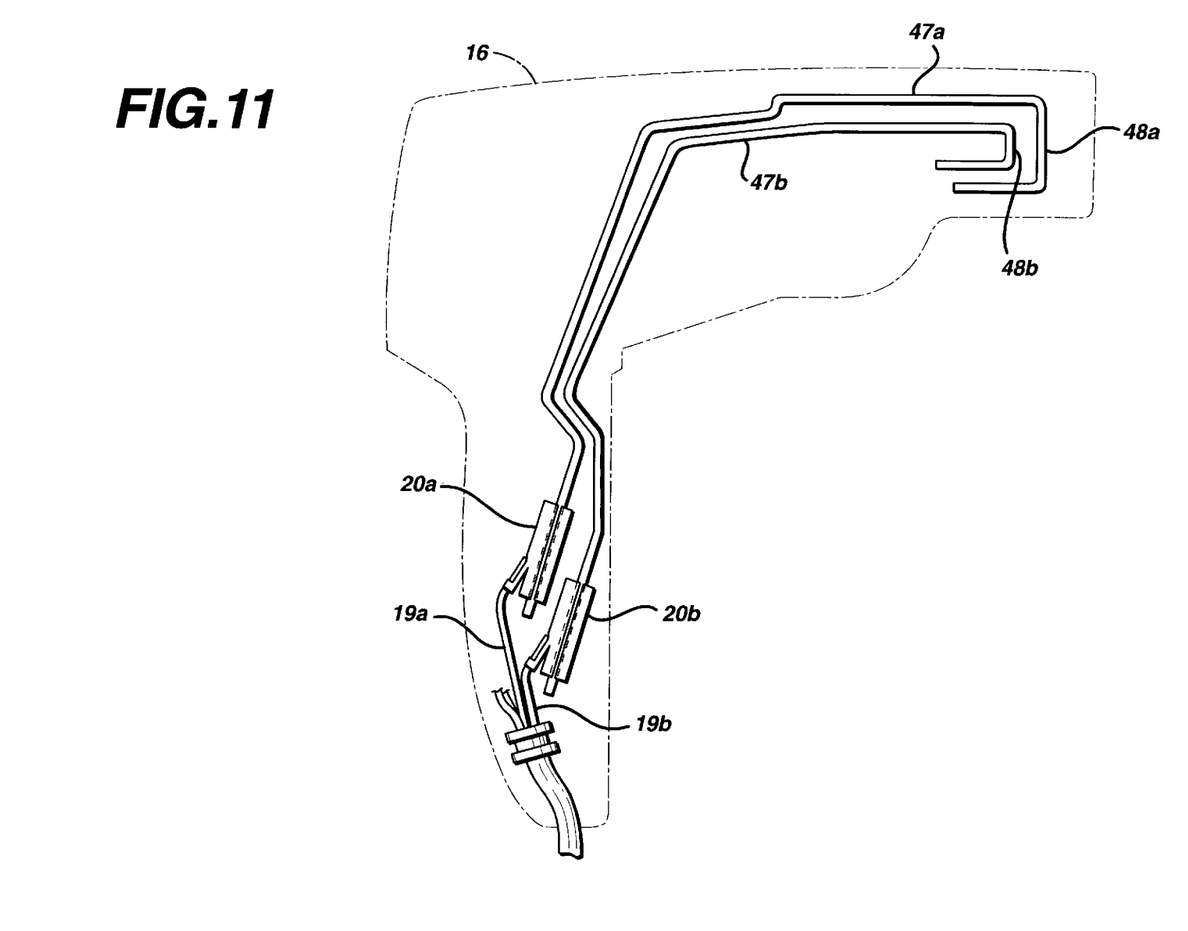
FIG. 11 is an elevational view of the inside of the left side handle portion showing the location of the wireforms and connectors used in the present invention.
Figure 12:
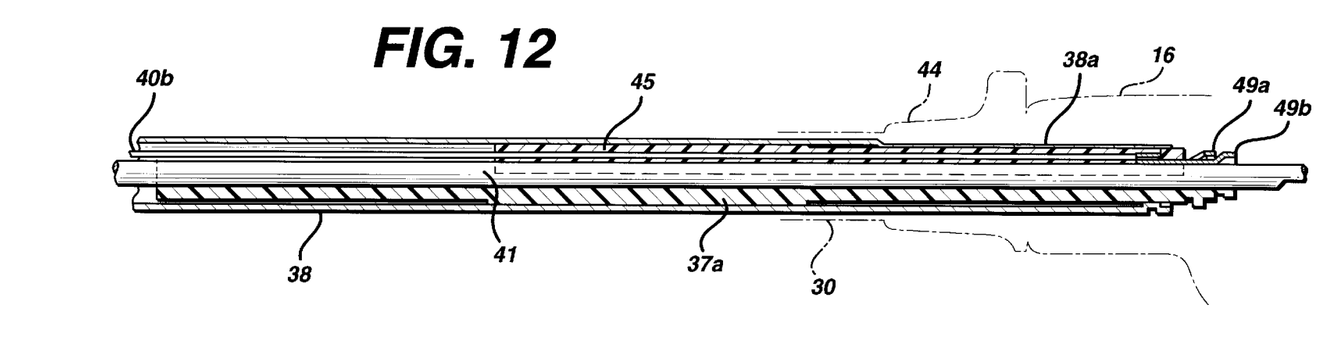
FIG. 12 is a longitudinal cross-sectional view of the intermediate portion of the instrument.
Figure 13:
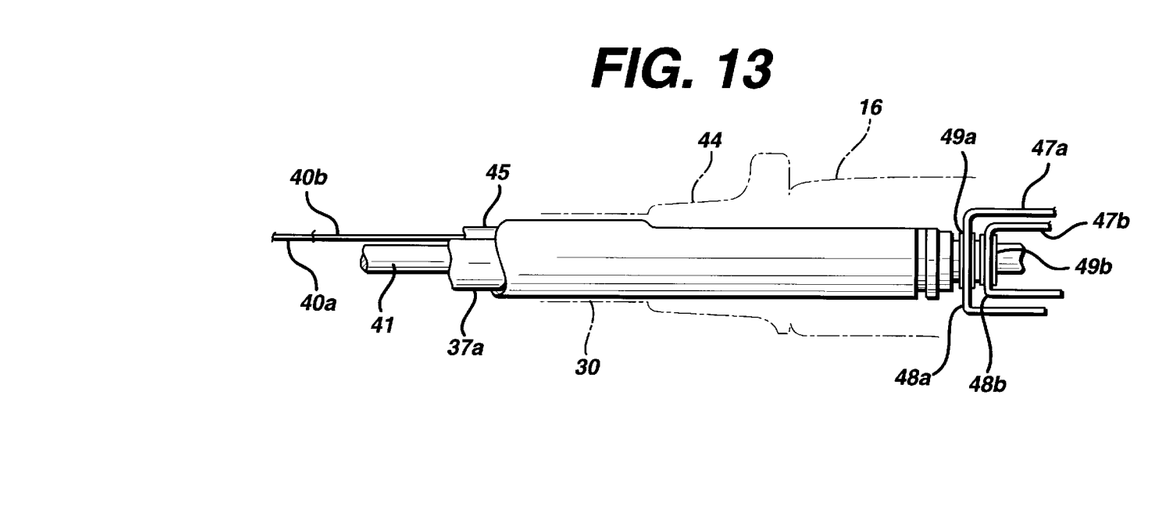
FIG. 13 is an elevational view of the proximal end of the intermediate portion showing the contact of the wireforms to their respective contact positions.
Figure 14:
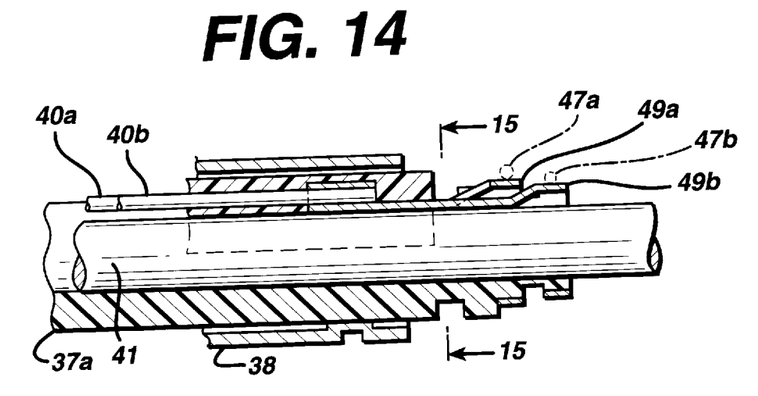
FIG. 14 is an enlarged cross-sectional view of the proximal end of the intermediate portion of the instrument.
Figure 15:
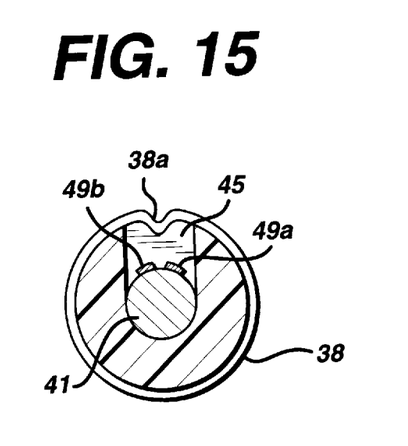
FIG. 15 is a transverse cross sectional view taken along the lines 15—15 of FIG. 14.
Figure 16:
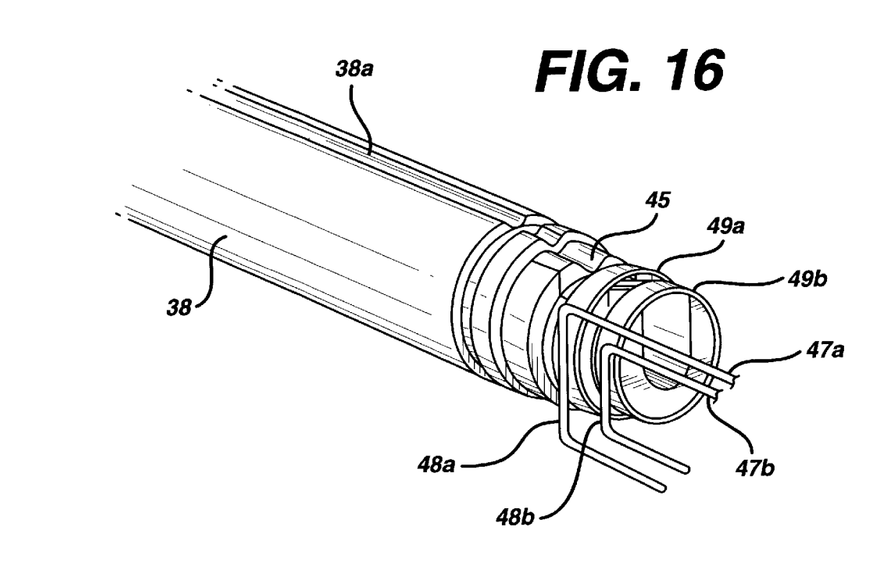
FIG. 16 is a perspective view showing the wireforms contacting their respective contact position.
Figure 17:
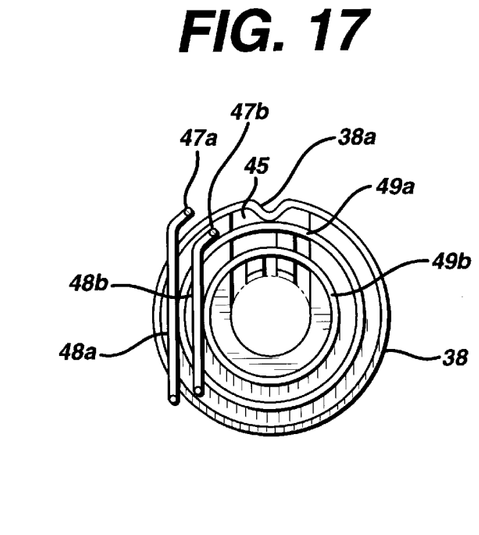
FIG. 17 is an end view of FIG. 16 showing a slight bias in the wireforms allowing for pressure of the wireforms onto their respective contact position.

Referring now to FIGS. 1–4, 8–17 there is illustrated an instrument of the present invention. FIGS. 5–7 illustrate an end effector of an alternative embodiment which may use similar electrosurgical energy delivery and actuation mechanisms.

Figure 1:
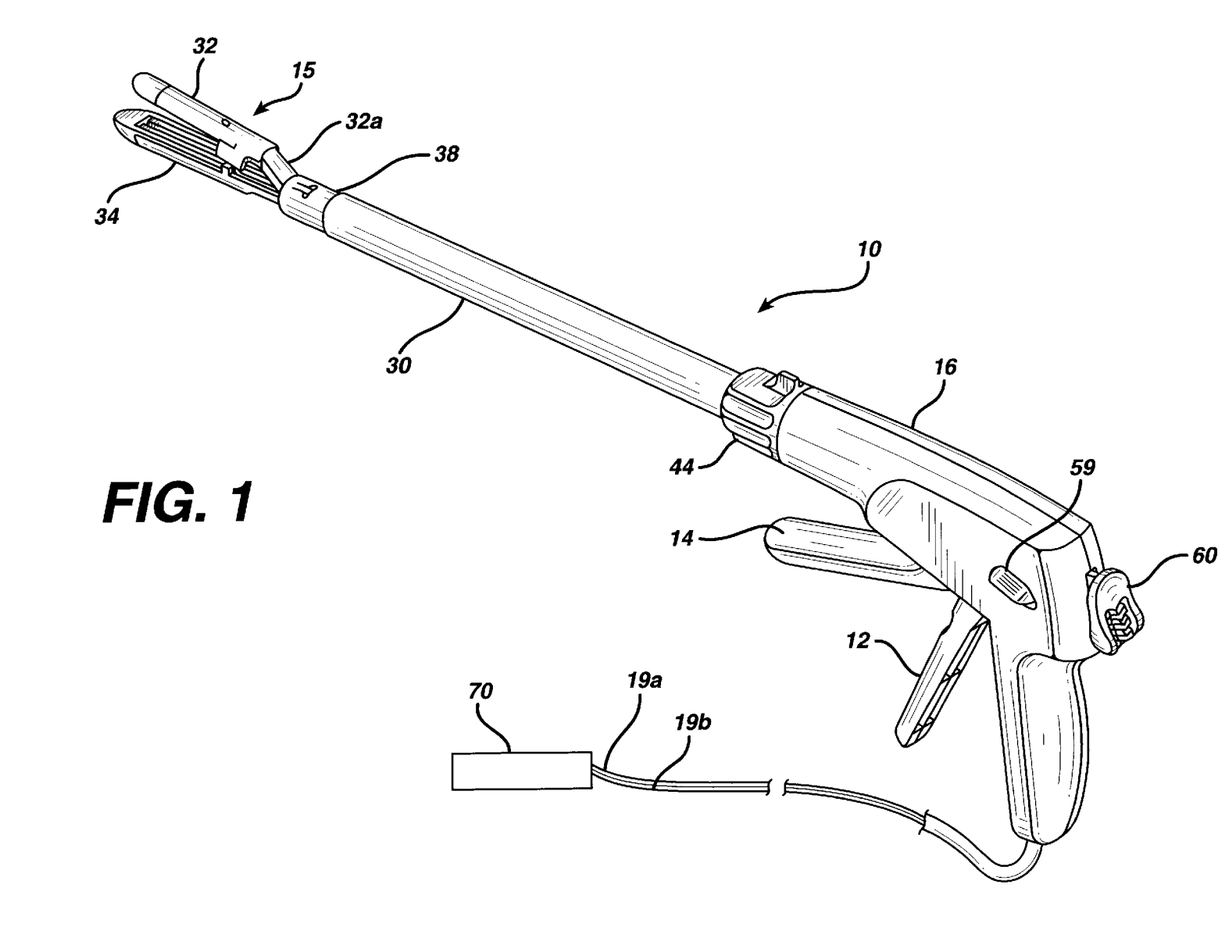
FIG. 1 is a perspective view of an endoscopic electrosurgical clamping and coagulating device of one embodiment of the present invention.

An endoscopic clamping and cutting instrument 10 is shown having a housing 16 coupled to a sheath 30 with a lumen extending therethrough and an end effector 15 extending from the distal end of the sheath 30. The end effector 15 comprises first and second jaw members 32, 34. Jaw member 32 is movably secured to jaw member 34. The housing 16 has a clamping trigger 12 for closing jaw members 32, 34, an RF switch detente arm 58 and electrical switch contacts 67a, 67b, coupled to an electrical switch 59 for turning on RF energy, and a firing trigger 14 for advancing the cutting element 11 through tissue.

Figure 2:
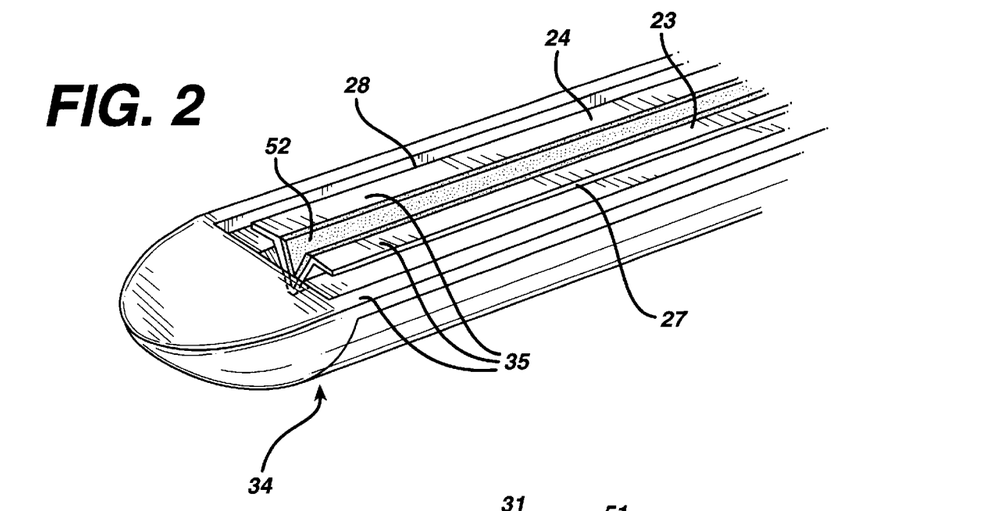
FIG. 2 is a bottom isolated view of the lower jaw of the clamping instrument of FIG. 1.
Figure 3:
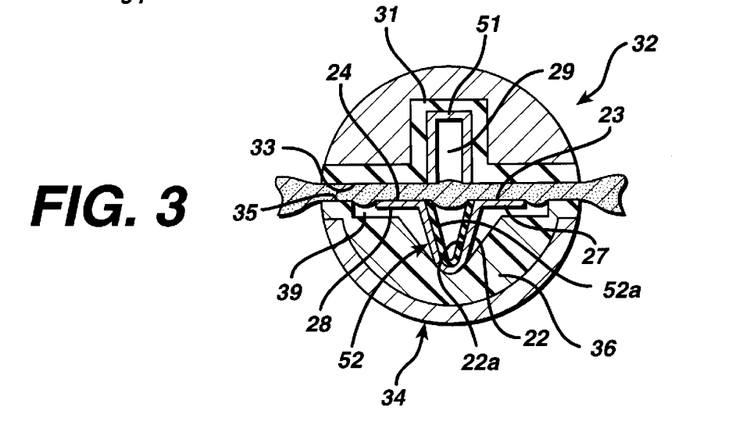
FIG. 3 is a front cross sectional view of the distal end of the instrument of FIG. 1 engaging relatively thin tissue.
Figure 4:
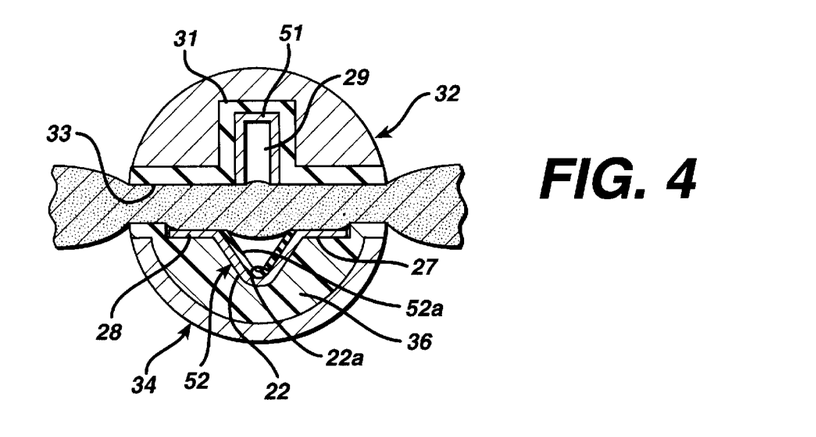
FIG. 4 is a front cross sectional view of the distal end of the instrument of FIG. 1 engaging relatively thicker tissue than that of FIG. 3.

Jaw member 32 comprises a U-shaped electrode 51 forming a knife channel 29 extending longitudinally through jaw member 32. An insulator 31 preferably formed of a polymer such as polyphenyleneoxide surrounds the electrode 51. Jaw member 32 has an inner surface 33 comprised of the electrode 51 and insulator 31. Inner surface 33 substantially faces an inner surface 35 of jaw member 34.

Jaw member 34 comprises an insulator 36 forming a portion of surface 35 and forming an indentation 39 on surface 35, and a spring electrode 52 inserted into the indentation 39. The electrodes 51, 52 are comprised of a conductor, such as, surgical grade stainless steel. Spring electrode 52 further comprises a layer of insulation 52a formed on its inner surface.

The electrode 51 acts as a first pole of a bipolar tissue treatment or therapeutic system. When the jaws 32, 34 are closed together the electrode 51 is electrically isolated from spring electrode 52 by the insulator 52a to prevent shorting by inadvertent contact of electrode 51 with spring electrode 52. The spring electrode 52 acts as a second therapeutic electrode of the bipolar treatment or therapeutic system, the electrode 52 being electrically opposite of the electrode 51.

The spring electrode 52 extends longitudinally, proximal to distal, within indentation 39 of jaw member 34 and comprises a V-shaped body 22 having flaps 23, 24 extending longitudinally through indentation and forming electrode bars 27, 28. The inner surface 22a of the body 22 is insulated by insulator 52a whereas the bars 27, 28 are exposed. The insulation may be made of an insulating polymer such as, for example, polyphenyleneoxide. The spring electrode 52 is biased in a closed v-direction.

When thin tissue is engaged by the jaw members 32, 34 (FIG. 3), the flaps 23, 24 tend to be closer together because the compressive force is not as great as when thicker tissue (FIG. 4) is engaged. When thicker tissue is engaged, the compressive force between surfaces 33, 35 is greater, causing the flaps 23, 24 to spread away from each other. Thus, when thinner tissue is engaged, the distance between electrode bars 27, 28 and electrode 51 is less than when thicker tissue is engaged.

In a preferred embodiment the device is used for a relatively thin more compressible, or fatty tissue such as mesentery tissue, or a relatively thick or more dense tissue such as muscular tissue or adnexa. Compressibility as used herein means the ability of tissue to compress in size upon application of a given force. Generally, fatty tissue tends to have a higher impedance, lower density and higher compressibility than muscular or adnexa tissue. The electrodes are arranged on interfacing surfaces to adapt to the expected tissue type. When thinner mesentery tissue is engaged, the current path or distance between the electrodes is shortened to decrease the relative impedance on the electrodes, whereas with thicker muscular or adnexa tissue, the distance is increased to increase the relative impedance as presented to the electrodes and thus the generator. Thus, in this embodiment, the adaptive electrodes decrease the differences in load impedance between two different tissue types.

The spring electrode 52 is arranged to continuously adapt to the change in tissue thickness and compression as the tissue is treated with electrosurgical energy. Typically, the tissue will become thinner as it is treated. The tissue also tends to increase in impedance as it coagulates. The spring electrode will move towards a closed-V position as the tissue becomes thinner or more compressed, thereby shortening the current pathway and thus lowering the impedance of the tissue and/or continuing to ensure electrical contact of tissue with the electrodes 51, 52.

An alternative embodiment of the end effector is illustrated in FIGS. 5–7. Jaw member 132 comprises an insulator 131 preferably formed of a polymer such as polyphenyleneoxide. Jaw member 132 includes a knife channel 129 extending longitudinally through it. Jaw member 132 has an inner surface 133 which substantially faces an inner surface 135 of jaw member 134.

Jaw member 134 comprises a channel 122 which is adapted to receive cartridge 123. The channel 122 comprises a U-shaped electrode 151 forming the outer circumference of the jaw member 134. A changeable cartridge 123 is inserted into the channel 122. The cartridge 123 comprises an insulator 139 and a U-shaped electrode 152 forming substantially parallel bar electrodes 127, 128 which comprise a portion of surface 135 and form compression ridges 156. The U-shaped electrode 152 is surrounded by the insulator 139.

The cartridge 123 may be interchangeable with cartridges having different electrode configurations adapted for particular tissue types, thicknesses and/or different applications. FIG. 6 illustrates the end effector of FIG. 5 engaging relatively thick adnexa tissue. The cartridge 123 has a narrow U-shaped electrode 152. Bars 127 and 128 are a distance $D_1$ from ridges 156 of electrode 152. FIG. 7 illustrates an end effector engaging relatively thin mesentery tissue. The end effector includes an alternative cartridge 123a having a wide U-shaped electrode 152a forming ridges 156a. Bars 127a and 128a are a distance $D_2$ from electrode 151 of electrode 152a where $D_1>D_2$. Cartridges 123 and 123a may be selected depending on the expected tissue thickness, compressibility, density, composition, or particular application of the device. The electrodes 151 and 152 or 152a may be connected to an energy source in a similar manner as the electrodes 51 and 52.

Referring again to FIGS. 1–4 and 8–17, the sheath 30 is formed of an insulative material and has a closure tube 38 extending through its lumen. A channel retainer 37a extends from the proximal end of the closure tube 38 and is secured to channel 37 which there extends distally through the remainder of the closure tube 38 to form jaw member 34. The channel 37 includes jaw member 34 extending distally from the closure tube 38.

The body 16 has a clamping trigger 12 for advancing the closure tube 38 to close the jaws 32, 34 towards each other engaging tissue therebetween. Rotation of the clamping trigger 12 causes the closure tube 38 to advance co-axially through the sheath 30 over a camming surface 32a of jaw 32 to close the jaws 32, 34 onto tissue situated between the jaws 32, 34.

The channel retainer 37a guides co-axial movement of a drive rod 41 within the channel 37. The drive rod 41 is advanced by the rotation of the firing trigger 14 as described in more detail below. The driving rod 41 is coupled on its distal end to a block 43. The block 43 is coupled to a cutting means 11 which the drive rod 41 advances by way of the block 43 into the end effector 15. Jaw member 32 is secured by way of the channel 37 to the jaw member 34.

When the drive rod 41 advances the cutting element 11, the cutting element 11 advances through the knife channel 29 in between the bars 27, 28 to cut tissue engaged by jaws 32, 34. This preferably occurs when the tissue has been electrosurgically treated. Thus, the cut line is medial to the coagulation lines formed by the bar electrodes 27, 28.

A knob 44 located on the distal end of the body 16 rotates the closure tube 38, channel retainer 37a, channel 37 and end effector 15 which are directly or indirectly coupled to the knob 44 so that the knob 44 may be used for rotational placement of the end effector jaws 32, 34. The knob 44 includes a peg (not shown) which fits into and engages indentation 38a closure tube 38. Closure tube 38 is fitted at its proximal end, into the housing 16.

Electrical energy is supplied to the electrode 51 and 52, by generator 70 through connections such as those described below, or other connections means, such as, for example, like those described in parent application Ser. No. 08/095,797, incorporated herein by reference. The generator 70 is user controlled by way of RF switch 59 located in the housing 16. Alternatively, a user controlled foot pedal may be used.

Wires 19a and 19b extend into the body 16 of the instrument and deliver energy to electrodes 51, 52 respectively. Wires 19a, 19b are coupled to low impedance contact elements 20a, 20b respectively and contact elements 20a, 20b are coupled to wireforms 47a, 47b respectively. Wireforms 47a, 47b are exposed at their distal ends 48a, 48b. Wireforms 47a and 47b are biased respectively towards contact ring 49a and contact ring 49b located on the proximal end of channel retainer 37a, so as to make electrical contact with the contact ring 49a and ring 49b respectively.

Wire 19a delivers electrical current to the electrode 51 by way of first wire form 47a which contacts contact ring 49a coupled to wire 40a extending through closure tube to electrode 51.

Wire 19b delivers electrical current to the electrode 52 through second wire form 47b which contacts contact ring 49b coupled to wire 40b extending through the closure tube 38 to the electrode 52.

The contact rings 49a, 49b permit the knob 44 to rotate while contact is maintained between ring 49a, ring 49b, and wireforms 47a, 47b, respectively. The ring 49a is electrically insulated from the ring 49b.

Wires 40a, 40b extend through seal 45 which fits into channel retainer 37a, which fits into closure tube 38.

Clamping trigger 12 includes gear teeth 12a which movably engage with teeth 66b of yoke 66. Yoke 66 is coupled on its distal end to the closure tube 38. When clamping trigger 12 is actuated, the gear teeth 12a engage with teeth 66b in yoke 66 causing the yoke 66 to advance distally. Closure tube 38 closes jaws 32, 34 as it advances over camming surface 32a of jaw 32.

The RF switch 59 is rotated to switch on RF energy to be supplied to the therapeutic electrodes 51, 52. When the RF switch 59 is rotated, detente protrusion 59a on the switch 59 hooks under detente protrusion 58a on detente arm 58, preventing the switch 59 from deactivating RF energy unless the RF switch 59 is manually rotated back to its original position. The RF energy may also be turned off electrically, e.g., in response to tissue impedance feedback.

Switch 59 has a moveable contact 67a and a stationary contact 67b. The moveable contact 67a rotates with switch 59 to contact stationary contact 67b when switch is on.

Ledge 60a of release button 60 is engaged with the proximal end of the yoke 66 adjacent step ledge 66a on proximal end of yoke 66. When the yoke 66 is advanced by the clamping trigger 12, the ledge 60a rotates down behind proximal end of yoke 66, thereby preventing yoke 66 from retracting until release button 60 has been pressed. Thus the jaws 32, 34 will remain in a closed position until a user releases the jaws 32, 34 with release button 60.

The switch 59 includes fingers 59c which sit just above proximal end of yoke 66. The ledge 60a of the release button 60 fits in between fingers 59c. The RF switch 59 cannot be activated, i.e., rotated forward, until the yoke 66 has been advanced distally so that fingers 59c of switch 59 are free to rotate behind proximal end of yoke 66.

The switch 59 also includes a lower hook 59b which engages groove 53a of firing rack 53. Firing rack 53 includes gear teeth 53b which are engaged by gear teeth 14a of firing trigger 15. The firing rack 53 is coupled on its distal end to pinion gear 54 which in turn engages the drive rod 41.

When the firing trigger 14 is pulled, the fire rack 53 is advanced distally to rotate pinion 54 which advances the driving rod 41 distally to actuate the cutting element 11 to cut tissue engaged by the end effector 15.

The firing rack 53 cannot advance however until the lower hook 59b of the RF switch is disengaged from the groove 53a of the firing rack 53. This occurs only when the RF switch 59 has been activated.

Thus, the presently described device includes a lockout device or devices for preventing application of RF energy, or knife actuation until the jaws 32, 34 have been closed. The lockout device(s) require the proper sequence is followed, i.e, jaw closure, followed by application of RF energy, followed by cutting element actuation. It also provides a detented RF switch so that RF energy is continuously applied until the switch 59 is manually released or until the RF energy is switched off, e.g., by an electrical feedback control signal to the generator 70.

The closure trigger 12 and firing trigger 14 are interlocked and a spring 57 is mechanically coupled to both triggers 12, 14.

When tissue is engaged between clamped jaw members 32, 34, and RF energy has been applied, the firing trigger 14 located on housing 16 may be actuated to advance a cutting element 11 through the engaged tissue to cut the tissue.

Several variations of this invention have been described in connection with specific embodiments. Naturally, the invention may be used in numerous applications where hemostasis or other electrosurgical tissue effects are desired. For example, the devices described herein may include a mechanism for cutting tissue and/or applying staples or other fasteners. See for example U.S. Ser. Nos. 095,797 and 096,154 incorporated herein by reference. Accordingly, it will be understood by those skilled in the art that various changes and modifications may be made in the invention without departing from its scope, which is defined by the following claims and their equivalents.

What is claimed is:

1. An electrosurgical device comprising:
    a handle;
    a first jaw member and a second jaw member connected to said handle by an actuator adapted to move said first jaw member with respect to said second jaw member;
    a first surface on one of said first and second jaw members including an elongated spring electrode which extends from a proximal portion of said one jaw member to a distal portion of said one jaw member.

2. An electrosurgical device according to claim 1 wherein said one jaw member comprises said first jaw member and said second jaw member includes a second electrode arranged on a surface of said second jaw member.

3. An electrosurgical device according to claim 1 wherein said one jaw member includes a second electrode arranged on a surface of said second jaw member.

4. An electrosurgical device having an end effector capable of receiving electrosurgical energy therein, said end effector comprising:
    first and second electrically insulated opposing interfacing surfaces, said interfacing surfaces capable of engaging tissue therebetween;
    a first spring electrode; and
    a second electrode insulated from said first spring electrode;
    wherein said first spring electrode is located on said first interfacing surface and said second electrode is located on one of said first and second interfacing surfaces.

5. The electrosurgical device of claim 4 wherein said first spring electrode is flexible and moves with respect to said second electrode from a first position to a second position.

6. The electrosurgical device of claim 5 wherein said first spring electrode moves as electrosurgical energy is applied to tissue.

7. The electrosurgical device of claim 4 wherein said first spring electrode is flexible such that, when said interfacing surfaces engage tissue, said first spring electrode and said second electrode are separated by a distance, said distance being a function of a parameter of said tissue engaged by said surfaces.

8. The electrosurgical device of claim 7 wherein said parameter is tissue composition.

9. The electrosurgical device of claim 7 wherein said parameter is tissue thickness.

10. The electrosurgical device of claim 7 wherein said parameter is tissue type.

11. The electrosurgical device of claim 7 wherein said parameter is tissue compressibility.

12. The electrosurgical device of claim 7 wherein said parameter is tissue density.

13. An electrosurgical device having an end effector capable of receiving electrosurgical energy therein, said end effector comprising:
    first and second electrically insulated opposing interfacing surfaces, said interfacing surfaces capable of engaging tissue therebetween;
    a first electrode;
    a second electrode insulated from said first electrode;
    a removable cartridge forming at least a portion of one of said interfacing surfaces, wherein said first electrode is located on said cartridge and said second electrode is located on one of said first and second interfacing surfaces.

14. The electrosurgical device of claim 13 wherein said cartridge is selectable from a plurality of cartridges, said cartridge adapted for use in a predetermined application.

15. The electrosurgical device of claim 13 wherein said cartridge is selectable from a plurality of cartridges, said cartridge adapted for use with tissue having a predetermined tissue parameter.

16. The electrosurgical device of claim 15 wherein said tissue parameter is electrical impedance.

17. The electrosurgical device of claim 15 wherein said tissue parameter is tissue composition.

18. The electrosurgical device of claim 15 wherein said tissue parameter is tissue compressibility.

19. The electrosurgical device of claim 15 wherein said tissue parameter is tissue density.

20. The electrosurgical device of claim 15 wherein said tissue parameter is tissue type.

21. The electrosurgical device of claim 15 wherein said tissue parameter is tissue thickness.

* * * * *

UNITED STATES PATENT AND TRADEMARK OFFICE
CERTIFICATE OF CORRECTION

PATENT NO. : 5,876,401
DATED : March 2, 1999
INVENTOR(S) : Dale R. Schulze, William D. Fox, David C. Yates, Anil Nalagatla It is certified that error appears in the above-identified patent and that said Letters Patent is hereby corrected as shown below:

On the title page item [*], delete "5,693,057" and insert --5,693,051--

Signed and Sealed this

Twenty-first Day of December, 1999

Attest:

Q. TODD DICKINSON

Attesting Officer     Acting Commissioner of Patents and Trademarks